(12) United States Patent
Schmidt et al.

(10) Patent No.: US 6,696,575 B2
(45) Date of Patent: Feb. 24, 2004

(54) BIODEGRADABLE, ELECTRICALLY CONDUCTING POLYMER FOR TISSUE ENGINEERING APPLICATIONS

(75) Inventors: Christine E. Schmidt, Austin, TX (US); Tyrell J. Rivers, Elkins Park, PA (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/107,705

(22) Filed: Mar. 27, 2002

(65) Prior Publication Data

US 2003/0066987 A1 Apr. 10, 2003

Related U.S. Application Data

(60) Provisional application No. 60/279,019, filed on Mar. 27, 2001.

(51) Int. Cl.[7] .................... C07D 295/00; C07D 207/00; H01B 1/12
(52) U.S. Cl. ........................................ 548/524; 252/500
(58) Field of Search ........................... 252/500; 548/524

(56) References Cited

U.S. PATENT DOCUMENTS

| | | | |
|---|---|---|---|
| 6,095,148 A | 8/2000 | Shastri et al. | 128/898 |
| 6,103,255 A | 8/2000 | Levene et al. | 424/426 |
| 6,224,893 B1 | 5/2001 | Langer et al. | 424/423 |
| 6,328,990 B1 | 12/2001 | Duchey et al. | 424/426 |
| 6,337,198 B1 | 1/2002 | Levene et al. | 435/174 |

Primary Examiner—Mark Kopec
(74) Attorney, Agent, or Firm—Gardere Wynne Sewell llp

(57) ABSTRACT

The subject matter of the present invention includes a novel biodegradable conducting polymer for biomedical applications. The polymer combines mixed heteroaromatic conductive segments of pyrrole and thiophene with flexible aliphatic chains via degradable ester linkages. In addition to its utility for peripheral nerve regeneration, the polymer may be applied to other areas of tissue engineering, including spinal cord regeneration, wound healing, bone repair, muscle tissue stimulation, and other regenerative, restorative, reconstructive, therapeutic, prophylactic, and diagnostic functions.

39 Claims, 6 Drawing Sheets

Scheme 1
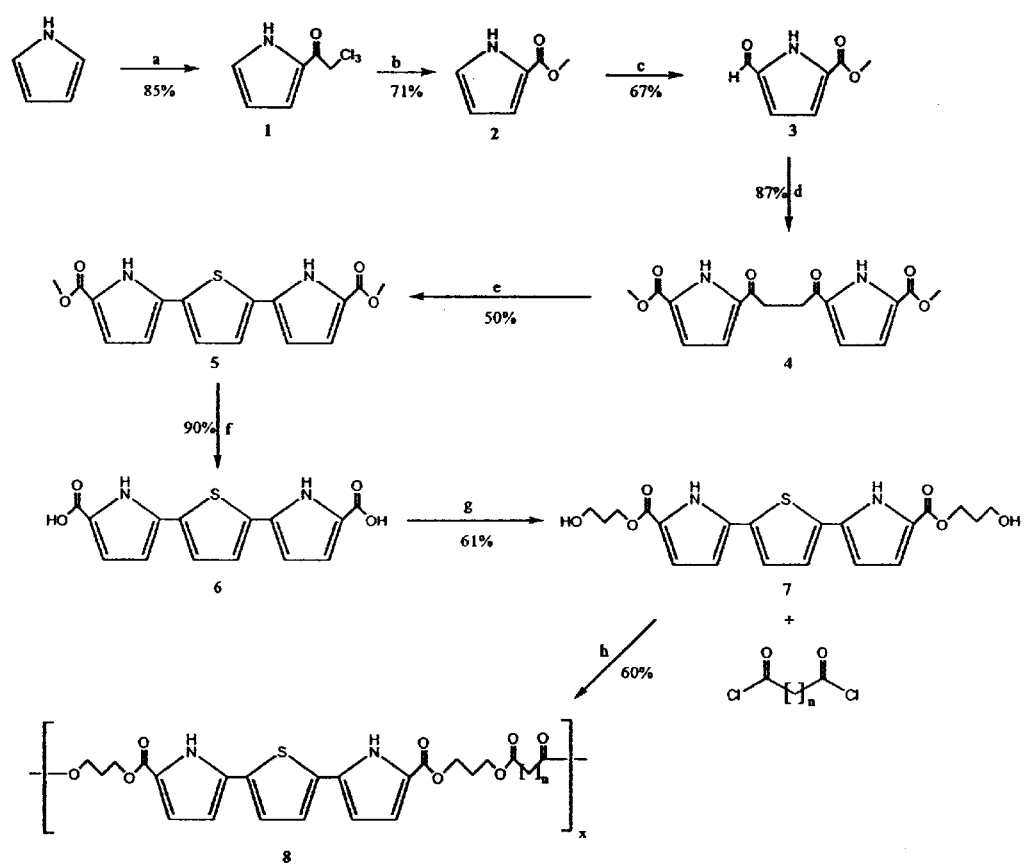

BIODEGRADABLE, ELECTRICALLY CONDUCTING POLYMER FOR TISSUE ENGINEERING APPLICATIONS

This application claims the benefit of U.S. Provisional Application Serial No. 60/279,019, filed on Mar. 27, 2001.

The U.S. Government may own certain rights in this invention pursuant to the terms of the National Science Foundation grant BES-9733156.

FIELD OF THE INVENTION

The present invention relates generally to the field of conducting polymers and specifically to an ester-linked polymer containing pyrrole and thiophene units that is biodegradable.

BACKGROUND OF THE INVENTION

Electrical charges and electrical fields have beneficial healing effects on various tissues, including bone, cartilage, skin and connective tissue, cranial and spinal nerves, and peripheral nerves. Other studies have suggested that applied electrical fields can lead to regression of tumors. Thus, potential clinical applications of electrical stimulation range from the enhancement of healing of bone fractures and damaged cartilage to the treatment of ulcers and pressure sores on diabetic and bed-ridden patients. Applications in the nervous system include the treatment of spinal cord injury, and plastic and reconstructive surgery, in which peripheral nerve grafts are currently required.

More importantly, biomaterials possessing electrical properties offer the key advantage of being able to locally stimulate a desired tissue. Several electroactive polymers exist including piezoelectric (e.g., polyvinylidene fluoride) and electrically conducting materials (e.g., polypyrrole (PP), and polythiophene). Since piezoelectric materials depend on small mechanical deformations to produce transient surface charges, the level and duration of focused stimulation cannot be controlled. In contrast, electrically conducting polymers readily permit external control over both the level and duration of stimulation. Thus strategies designed to enhance the regeneration of a responsive cell might employ electrically conducting polymers.

There is currently no effective treatment for damage to central nervous system (CNS) nerves or for absolute tissue regeneration, although drugs can reduce swelling and damage to the tissue such as the spinal cord. In contrast to spinal cord injury, there exist therapies, although not optimal, for the treatment of damaged peripheral nerves. Current clinical treatments for peripheral nerve injury are surgical end-to-end anastomoses and autologous nerve grafts. Surgical end-to-end repair involves the direct reconnection of individual nerve fascicles and is useful only if nerve ends are directly adjacent, as tension in the nerve cable prohibits regeneration. To repair a nerve over a gap, autologous nerve grafts are used to physically guide the regenerating axons and to prevent the infiltration of occluding connective tissue. Unfortunately, there are several disadvantages to such nerve grafts, including loss of function at the donor site, mismatch of nerve cable dimensions between the donor graft and recipient nerve, and the need for multiple surgeries.

In an effort to surpass limitations of current treatments for peripheral nerve damage and to overcome the barriers to CNS regeneration, researchers are investigating the use of nerve guidance channels (NGCs) to bridge the gap between damaged nerve ends in the peripheral nervous system (PNS) and CNS. NGCs help direct axons sprouting off the regenerating (proximal) nerve end, provide a conduit for diffusion of neurotrophic factors secreted by the damaged nerve ends, and minimize infiltrating fibrous tissue that may impede regeneration. Several strategies to engineer an ideal NGC have been proposed, including the use of natural collagen matrices and the use of synthetic biomaterials such as polylactic acid. Synthetic materials, as opposed to natural counterparts, can be designed to incorporate a wide variety of well-defined features that enhance nerve regeneration. For example, growth factor release, permeability, and electrical conductivity have been shown to promote the regeneration of nerves. In addition, properties such as biodegradation, mechanical strength, and ease of material processing can be readily addressed using synthetic constructions. Thus, materials possessing these qualities will be most attractive for use in tissue engineering therapeutics in general, and specifically for a nerve graft alternative.

As already mentioned, electrical charges play an important role in stimulating either the proliferation or differentiation of various cell types such as osteoblasts (bone cells) and nerves. To take advantage of the beneficial effect of electrical stimulation on tissue regeneration, such as nerve, skeletal, or other living tissue, researchers have explored the utility of the piezoelectric polymer polyvinylidine-difluoride (PVDF) and poled polytetrafluoro-ethylene (PTFE). Both electroactive polymers promote enhanced neurite outgrowth in vitro and enhanced nerve regeneration in vivo. This effect has been attributed to either transient or static surface charges in the material. Synthetic scaffolds have been proposed for tissue repair and regeneration.

There remains a need, however, for biodegradable and bioactive polymers for tissue engineering that stimulate both tissue repair and regeneration. In addition, despite past research efforts in nerve regeneration, there still exists a need for a clinically attractive alternative to nerve or vein autografts.

SUMMARY OF THE INVENTION

The subject matter of the present invention includes a novel biodegradable conducting polymer for biomedical applications. The terms "conducting polymer" and "electrically conducting polymer" are used interchangeably in this application. The polymer combines mixed heteroaromatic conductive segments of pyrrole and thiophene with flexible aliphatic chains via degradable ester linkages. In addition to its utility for peripheral nerve regeneration, the polymer could also be applied to other areas of tissue engineering as well, such as spinal cord regeneration, wound healing, bone repair, and muscle tissue stimulation.

In one form, the present invention is a chemical compound having the general structure:

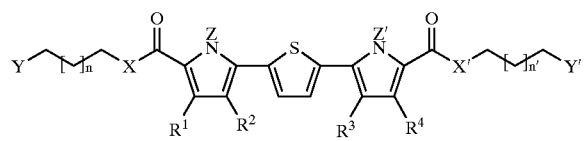

where n and n' are independently from 0 to 10 methylene units, and $R^1$, $R^2$, $R^3$ and $R^4$ are each independently a substituent selected from the group consisting of hydrogen, alkyl, aryl, halogen, hydroxyl, carboxyl or a salt thereof. X and X' are independently oxygen or nitrogen atoms that form ester or amido linkages, respectively; and Y and Y' are independently an OH or a $NH_2$ substituent; and Z and Z' are each independently a substituent selected from the group consisting of hydrogen, alkyl, aryl, halogen, hydroxyl, carboxyl or a salt thereof.

The present invention may also be a biodegradable conducting polymer for tissue engineering using the chemical compound described above. For example, the present invention also includes the synthesis of a compound for use in the preparation of a biodegradable conducting polymer according to the SCHEME:

wherein n=1 to 10.

In yet another form, the present invention is a method for stimulating cell response by contacting a conducting polymer with a repeating unit of the formula:

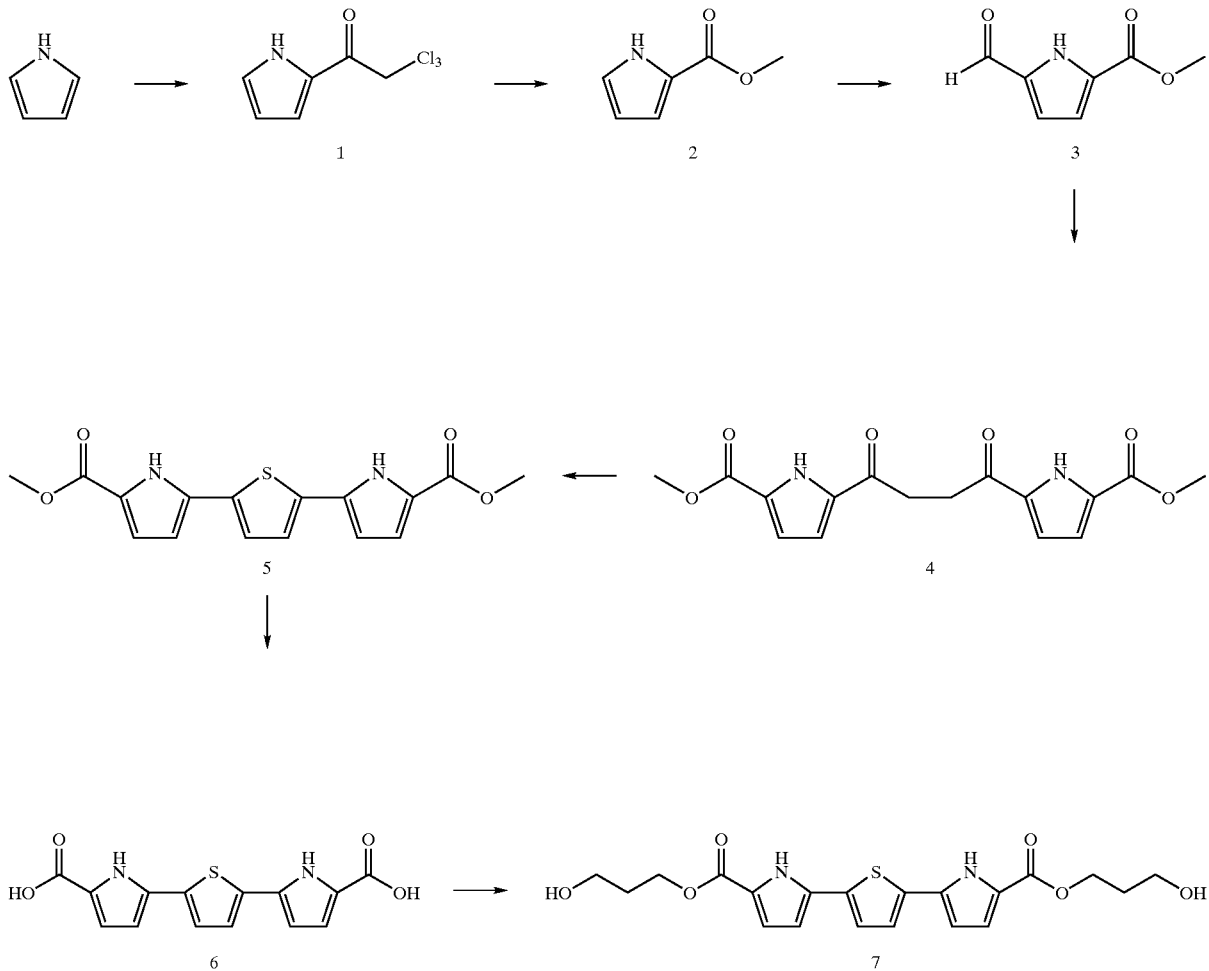

In another form, the present invention is a biodegradable conducting polymer prepared by the method described above. The present invention is a method for preparing a conducting polymer by reacting compound 7 (SCHEME 1) with a diacid chloride to form compound 8 (SCHEME 1).

The present invention also includes a method for the synthesis of a biodegradable conducting polymer according to SCHEME 1 and the biodegradable electrically conducting polymer produced by the method.

The present invention may also be a biodegradable conducting polymer with a repeating unit of the following structure:

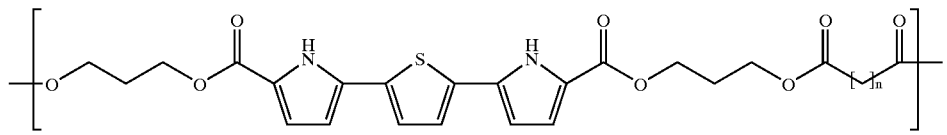

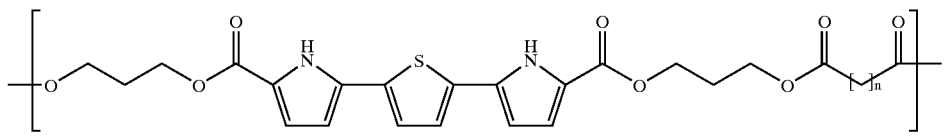

where n=1 to 10 with one or more cells and applying an electrical current of sufficient power to stimulate but not harm the cells.

BRIEF DESCRIPTION OF THE DRAWINGS

The above and further advantages of the invention may be better understood by referring to the following description in conjunction with the accompanying drawings in which corresponding numerals in the different FIGURES refer to the corresponding parts in which.

DETAILED DESCRIPTION OF THE INVENTION

While the making and using of various embodiments of the present invention are discussed herein in terms of compounds for use in a conducting polymer, a conducting polymer that can used to stimulate cells response and methods for preparing these compounds, it should be appreciated that the present invention provides many inventive concepts which can be embodied in a wide variety of specific contexts. The specific embodiments discussed herein are merely illustrative of ways to make and use the invention are not meant to limit the scope of the present invention in any way.

Terms used herein have meanings as commonly understood by a person of ordinary skill in the areas relevant to the present invention. Terms such as "a," "an," and "the"are not intended to refer to only a singular entity, but include the general class of which a specific example may be used for illustration. The terminology herein is used to describe specific embodiments of the invention, but their usage does not limit the invention, except as outlined in the claims.

All technical and scientific terms used herein have the same meaning as commonly understood by one of ordinary skill in the art to which this invention belongs, unless defined otherwise. Methods and materials similar or equivalent to those described herein may be used in the practice or testing of the present invention, the generally used methods and materials are now described.

Figure 1:
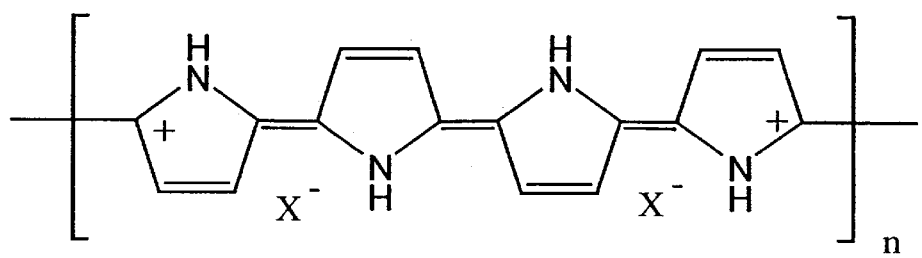
FIG. 1 depicts polypyrrole in its conductive state.

Oxidized polypyrrole (PP) (FIG. 1) has been evaluated for use as a matrix for nerve cell adhesion and neurite outgrowth in culture, and for use in nerve guidance channels (NGCS) to support regeneration of the rat sciatic nerve across a 10-mm defect. PP was selected for study because of its inherent electrical conductivity, its ease of preparation, its good cell compatibility, and most importantly, its ability to stimulate a nerve locally. In addition, compared to other electrically conducting polymers, PP has been the extensively investigated for use in biological systems.

There are advantages of using PP in medical applications. First, unlike exogenous electromagnetic fields that cannot accurately confine stimulation, electrical conduction is channeled through PP, allowing precise localization of the stimulus to the desired nerve. Second, unlike piezoelectric materials that require small mechanical deformations to generate surface charges, PP offers the ability to externally control stimulation. Although piezoelectric materials may hold promise for nerve regeneration, the ability to externally regulate the level and duration of electrical stimulation such as with PP should prove advantageous.

Previous studies have demonstrated that PP can support in vitro attachment and differentiation of PC-12 cells (a well-characterized neuronal cell line) and primary nerve cell explants. In addition, it has been shown that these nerve cells extended longer neurites on PP films compared to FDA-approved polymers such as poly(lactic acid) and poly(lactic acid-co-glycolic acid). Moreover, a significant enhancement in neurite length (versus unstimulated controls) has been observed when an electrical stimulus is applied. This result compared favorably with similar studies using poled piezoelectric materials. Beneficial effects from PP have also been demonstrated in animal implantation studies where PP provoked little adverse tissue response compared to the PLGA and enhanced baseline nerve regeneration across a gap of silicone controls. Taken together, these studies suggest that PP is an attractive material for biomedical applications.

Unfortunately, PP in its present form (FIG. 1) is not easily processed into various forms and is non-biodegradable. Although several applications that exploit the electronic conductivity (glucose sensors) and reversible electrochemistry (dopamine release) of PP have been proposed and explored, these applications could be optimized if only the polymer were reasonably processable. In tissue engineering, the control over three-dimensional architecture in a predictable fashion is crucial to elicit desired cellular responses. Hence, the synthesis of a processable and pliable electrically conducting polymer would be an enormous contribution. Furthermore, although PP appears to exhibit good tissue compatibility, it would be desirable if it were biodegradable as well. With biodegradation, the degraded material would either be, for example, excreted or absorbed by the body to leave behind only native tissue. The long-term presence of any foreign material always poses a potential risk. This is especially true for nerves, where compression of the nerve by NGCs has been cited as a problem. As a result of the possible dangers associated with permanent materials, the use of biodegradable biomaterials in clinical applications has become increasingly attractive.

Recent studies of conducting materials, such as polypyrrole and polythiophene, have focused on oligomers of these high molecular weight materials as model systems. These analogues have demonstrated similar electrochemical, optical, and electrical properties as their parent polymers. In addition, these oligomers can be functionalized and polymerized with other monomers to incorporate a variety of features such as increased solubility and processibility. For example, Hong and Miller synthesized an electrically conducting copolymer by coupling quaterthiophene oligomers with aliphatic segments. The potential for these polymers as biomaterials is enormous. However, these systems have been typically used for electronics and electrooptics and have not been explored for their ability to stimulate cellular processes and to biodegrade into nontoxic materials. Thus, a significant motivation exists to use electrically conducting oligomers to create polymers that are biodegradable and readily processed for biomedical and tissue engineering applications.

The subject matter of the present invention includes a novel electrically conducting polymer that incorporates processible and biodegradable features. Synthesis of the novel electrically conducting polymer is achieved by functionalizing pyrrole-thiophene-pyrrole units with alcohol groups and reacting this compound with an aliphatic diacid chloride. The design parameters include:

Choosing the Mixed Heteroaromatic Oligomer Chain Length

In electrochemically synthesized PP and polythiophene films, the conjugation length (delocalization of the positive charges) is typically 3–5 pyrrole/thiophene units. Beyond this length, the conjugation is disrupted as the result of a defect, possibly in the form of a C—C inter or intra-chain bond from radical coupling. This would suggest that a minimum chain of approximately this length would be sufficient to impart the necessary conductivity. In addition, PP and polythiophene films require oxidation before conductivity can be achieved. Oligomers of thiophene have been shown to maintain a stable oxidized state with only two units connected together. Furthermore, increasing the chain length in oligopyrroles, oligothiophenes, and mixed heteroaromatic oligomers results in a more stable oxidized compound.

Conductivity with polypyrrole and polythiophene results from the movement of electrons between chains (inter chain). Oligomers of thiophene have also demonstrated conductivity through a π-stacking phenomenon, which allow electrons to travel between chains. Thus, oligomers modified to incorporate features such as degradable linkages and flexible segments should remain conductive.

Choosing the Ester Linkage for the Polymer

The ester linkage can be enzymatically cleaved by esterases or by hydrolysis in the body. Degradation times for polyesters are variable (weeks to years) and are dependent on several parameters including the implantation site, mass and shape of implant, and polyester chemistry.

Polyesters are currently in wide use for several clinical applications including laryngeal prosthesis, ureter tubings, sutures, and blood vessel repair.

Variation in the diacid chloride chain length can be used to control several useful polymer properties such as degradation rate, wettability and mechanical strength.

Ester linkages can be enzymatically degraded by esterases or by hydrolysis. The breakdown products of compound 8 will yield 1,3-propanediol, hexanoic acid, and 2,5-bis(5-(hydroxycarbonyl)-2-pyrryl)thiophene (compound 6). The first two breakdown products should not be toxic to the body. Propanediol and hexanoic acid have one-half lethal dose (LD50) values for oral administration of 5 g/kg (mouse) and 3 g/kg (rat), respectively. These values are comparable to ethanol (7 g/kg for rat). Because of the dominance of pyrrole in the structure, we expect the product 2,5-bis(5-(hydroxycarbonyl)-2-pyrryl)thiophene to behave in a nontoxic manner similar to polypyrrole.

Thus, a biomaterial that couples the beneficial stimulatory effects of PP with the clinically-desired properties of biodegradation and flexibility would be useful for nerve regeneration therapies, and for other tissue engineering applications including regeneration of bone, cartilage, and skin as further discussed below Polymer Compositions and Delivery The biodegradable conducting polymer is delivered to the body in the form of a structure selected from the group consisting of sutures, tubes, sheets, films, and scaffolds. Scaffolds, sutures, tubes, and sheets, herein referred to as "scaffolds" are prepared from solutions of the biodegradable conducting polymer in a mixture of a solvent. The solutions are cast and phase separated followed by leaching using procedures known to those skilled in the art. Alternatively, the scaffolds may be comprised of ultrathin multilayer films prepared by one or more methods apparent to those skilled in the art. The fabrication method that may be used includes one or a combination of the those readily apparent to one skilled in the art, such as solution casting, Langmuir-Blodgett technique, chemisorption, depositing onto charged surfaces, coating onto another surface (e.g., fibers), casting of preformed layers, deposition of layer-on-layer, and annealing layers.

The scaffolds may consist of only the polymer or may be a polymer composition (generally with covalently crosslinkable polymers in combination with an effective, non-toxic initiator), or as blends of the biodegradable conducting polymer with one or more covalently and ionically crosslinkable or hydrophilic polymer with or without cells.

Suitable hydrophilic polymers for use with the biodegradable conducting polymer of the present invention include but are not limited to synthetic polymers such as poly(ethylene glycol), poly(ethylene oxide), partially or fully hydrolyzed poly(vinyl alcohol), poly(vinylpyrrolidone), poly (ethyloxazoline), poly(ethylene oxide)-co-poly(propylene oxide) block copolymers (poloxamers and meroxapols), poloxamines, carboxymethyl cellulose, and hydroxyalkylated celluloses such as hydroxyethyl cellulose and methylhydroxypropyl cellulose, and natural polymers such as polypeptides, polysaccharides or carbohydrates such as Ficoll® polysucrose, hyaluronic acid, dextran, heparan sulfate, chondroitin sulfate, heparin, or alginate, and proteins such as gelatin, collagen, albumin, or ovalbumin or copolymers or blends thereof. As used herein, "celluloses" includes cellulose and derivatives of the types described above; "dextran" includes dextran and similar derivatives thereof.

The blend of polymers may form a hydrogel or matrix using a material such as a carbohydrate polymer or polysaccharide (e.g., hyaluronic acid) in the presence of an initiator such as mono-, di- or trivalent cations or anions in water, a radical, or a photoinitiator. The polymer blend may be intrinsically biodegradable, biocompatible, or of sufficiently low molecular weight to allow excretion. Some components of the polymer blend exhibit little to no ability to biologically degrade. Where there are two or more water-soluble polymer blocks joined by other groups, the joining groups may include biodegradable linkages, polymerizable linkages, or both.

For use in mammals, the biodegradable conducting polymer scaffold may include one or more different types of cells and may also be used for tissue engineering. These cells may be obtained direct from a donor, from cell culture of cells from a donor, or from cell culture. Donor cells are generally obtained by biopsy and grown to confluence in culture using standard conditions apparent to those of skill in the art. The donor or cells obtained from the donor may be immunosuppressed as needed, for example, using a schedule of steroids and other immunosuppressant drugs, if required. This may provide immunoprotection of cell transplants while a new tissue or tissue equivalent is growing by excluding the host immune system. In addition, the present invention may be used to provide multiple cell types, including genetically altered cells, clones or transplants, within a three-dimensional scaffold for the purpose of transplant engraftment, immunotherapy, cognitive function, tissue regeneration, repair or reconstruction. Examples of cells include, but are not limited to, chondrocyte, osteoblast, muscle cell, thyroid cell, parathyroid cell, immune cell, pancreatic cell, fibroblast, hepatocyte, epithelial cell, islet cell, nerve cell, and other cells acting primarily to synthesize and secrete or metabolize materials, as well as biopsied or cloned cells of the intestines, kidney, heart, brain, spinal cord, muscle, skeleton, liver, stomach, skin, lung, reproductive system, nervous system, immune system, spleen, bone marrow, lymph nodes, glands.

Alternatively, the biodegradable conducting polymer of the present invention as well as scaffolds prepared with the biodegradable conducting polymer of the present invention are bioactive and formulated with one or more active species so that the biodegradable conducting polymer or scaffold becomes a microcarrier for one or more active species. The active species may be incorporated into the polymer or polymer solution (e.g., scaffold) or may be attached to its surface using techniques readily apparent to those skilled in the art. In some instances, it may be preferred to incorporate or attach the inactive version of the species that can then be activated to the active species as needed and required. The active species may be a drug or other biologically active compound; thus the scaffold may be a microcarrier for the delivery of drugs or other biologically active compounds when used in the body. Examples of biologically active compounds are proteins, peptides, polysaccharides, nucleic acids, oligonucleotides, natural and synthetic organic or inorganic molecules, and those biologic molecules used for therapeutic, prophylactic or diagnostic purposes. Drugs may include antibiotics, antivirals, chemotherapeutic agents, anti-angiogenic agents, hormones, anti-inflammatory agents, drugs having an effect on vascular flow or that are effective against one or more diseases, and combinations thereof.

The biodegradable conducting polymer of the present invention as well as the scaffold prepared with the biodegradable conducting polymer may be selectively combined with both cells and/or bioactive compounds (i.e., active species) to promote tissue/limb reconstruction, tissue regeneration, or tissue/cell/limb transplantation and engraftment. For example, a polymer matrix with cells may be combined with one or more active species such as angiogenic factors, antibiotics, anti-inflammatories, growth factors, alone or in combination with other compounds that induce differentiation and/or cell and tissue growth. In one method of attaching the active species to the biodegradable conducting polymer or scaffold (with or without cells), the active species (generally in its purifed form) in a buffered solution is placed on the polymer or scaffold for at least 24 hours. Non-adsorbed molecules are washed off prior to use. Alternatively, molecules may be dried directly onto the surface or cross-linked to the polymer or scaffold (with or without cells). For example, humoral factors may be mixed in a slow-release form with the cell-polymer suspension prior to its implant or transplantation. Alternatively, the polymer matrix may be modified to bind humoral factors or signal recognition sequences prior to its combination with a suspension of cells.

Use of the biodegradable conducting polymer of the present invention and the scaffold prepared with the biodegradable conducting polymer includes implantation and injection. When used to treat mammals such as cells, repair tissue, promote regeneration, replace damaged cells, enhance growth, proliferation, and differentiation or for transplantation, reconstruction, and improved tissue, organ or limb function, the effectiveness of the biodegradable conducting polymer and/or scaffold (including the cells and/or active species components if applicable) can readily be optimized by those skilled in the art without undue experimentation.

The biodegradable conducting polymer or scaffold may be implanted with materials that include sutures, tubes, sheets, adhesion prevention devices, wound healing products, tissue healing agents and other tissue or cell growth promoters that further enhance the effectiveness of treatment. In addition, a voltage or current may be applied directly to the biodegradable conducting polymer or scaffold or be externally applied at the repair, implant, transplant or reconstruction site. For diagnostic purposes, the biodegradable conducting polymer or scaffold may be incorporated not only with active species but also with one or more detectable agents or molecules at one of more sites in a mammal that allows for the diagnosis, monitoring, and prophylaxis of the site. Examples of agents include dyes, labels, metals, detection devices, and electronic chips.

Thus, the methods used to prepare the biodegradable conducting polymer of the present invention and the composition of the biodegradable conducting polymer of the present invention serve several beneficial functions when used in mammals, including regenerative, restorative, reconstructive, therapeutic, prophylactic, and diagnostic.

EXAMPLES

Reagents and solvents were purchased from Aldrich Chemical Co. and used as received. Toluene and tetrahydrofuran (THF) were dried by refluxing with sodium benzophenone ketyl under nitrogen. Pyridine and dichloroethane were dried by distillation under nitrogen from $CaH_2$ and stored over 4A molecular sieves. Pyrrole and phosphorus oxychloride were purified by distillation under nitrogen before use.

$^1$H-NMR and $^{13}$C-NMR spectra were obtained using a Varian Ultra Plus (300 MHz and 75 MHz, respectively) spectrometer. UV-visible spectra were recorded on a Beckman (DU 530) spectrophotometer. Gel permeation chromatography measurements were performed using a Viscotek Model 250 refractometer, a Waters 515 HPLC pump, and a series of two columns (10M-mixed-B-98A-6, Polymer Laboratories) in THF. To measure polymer conductivity, a groove was placed in a gold-coated slide such that no conductivity could be measured when the electrodes contacted opposite sides of the groove. A polymer film was cast (from dissolved THF) into the groove, forming a bridge between the gold surfaces. The slide was exposed to iodine vapor and an order of magnitude resistance was determined. Cyclic voltammetry (CV) measurements were performed using a CH-Instruments Electrochemical Detector (Model CHI832) in a nitrogen-filled glove box. The three-electrode electrochemical cell consisted of platinum working and counter electrodes (a thin polymer film was cast on the working electrode) and a zero leak Ag/AgCl reference electrode (Cypress Systems) at a scan rate of 100 mV/s (values were corrected to SCE). The electrolyte contained 0.2 M tetrabutylammonium tetrafluoroborate in dry acetonitrile. Prior to use the working electrodes were polished with 1 micrometer particle-size alumina slurry, sonicated for five minutes in deionized water, and exposed to a 25W oxygen plasma (1.75 torr) for five minutes. Thin polymer films were then spin-coated on the electrode using a Pine Instruments Rotator at 1000 rpm.

For biocompatibility studies, polymer films were spin-coated onto a glass slide (THF solvent) using a Pine Instruments Rotator at 7000 rpm. The films were vacuum dried at 50 degrees Centigrade overnight and then soaked in deionized water for another day to ensure complete removal of THF. Plastic wells were attached to the polymer surface using silicone rubber and these assemblies were vacuum dried again overnight. After rinsing the well with deionized water, the films were sterilized under UV for 1.5 hours. Human neuroblastoma cells (SK-N-SH, ATCC) were seeded on the polymer in Eagle minimum essential medium (EMEM) with 2 mM L-glutamine and Earles BSS adjusted to contain 1.5 g/L sodium bicarbonate, 0.1 mM non-essential amino acids, 1.0 mM sodium pyruvate, and 10% fetal bovine serum. These wells were placed in sterile petri dishes and cultured in a 37 degrees Centigrade and 5% $CO_2$ environment. Images were captured using an Olympus IX70 inverted microscope connected to an Optronics Magnafire camera (Model S60800).

2-(Trichloroacetyl)pyrrole (compound 1). To a mixture of anhydrous ether (130 mL) and trichloroacetyl chloride (95 mL; 0.85 mol) under a nitrogen purge was added pyrrole (50.03 g, 0.75 mol) dissolved in anhydrous ether (400 mL) via a dropping funnel over a 2-hour period. The now violet ether solution began to reflux slightly during addition. Refluxing was continued for an additional 1 hour before the reaction was quenched slowly with a solution of $Na_2CO_3$ (65 g) in water (200 mL). The layers were separated, and the red organic layer was washed four times with water and once with brine and finally dried over $Na_2SO_4$. The red ether solution was then treated twice with Norite (5 g) and filtered through Celite. The solvent was removed under vacuum to give the title compound (134.7 g, 0.63 mol, 85%). $^1$H-NMR ($CDCl_3$): δ 9.65 (br s, 1H), 7.40 (m, 1H), 7.18 (m, 1H), 6.39 (dd, 1H).

Methyl Pyrrole-2-carboxylate (compound 2). Sodium metal (6.9 g, 0.30 mol) was dissolved in anhydrous methanol (1.5 L) and then 2-(trichloroacetyl)pyrrole (223 g, 1.5 mol) dissolved in anhydrous methanol (500 mL) was added. The mixture was heated at reflux for 12 hour. The methanol was removed under reduced pressure and the product crystallized by pouring the residue into a 3:1 ice-water/methanol mixture (2 L). The light brown solid was collected by vacuum filtration and dried to afford 97.2 g (0.78 mol, 74%) of the title compound. $^1$H-NMR ($CDCl_3$): δ 7.00 (m, 1H), 6.79 (d, 1H), 6.15 (dd, 1H), 3.74 (s, 1H).

Methyl 5-Formylpyrrole-2-carboxylate (compound 3). Anhydrous DMF (7.0 mL, 90.4 mmol) was cooled to 5–10 degrees Centigrade under nitrogen. $POCl_3$ (7.8 mL, 83.7 mmol) was added dropwise to the cooled DMF over a couple of minutes. Dry 1,2-dichloroethane (25 mL) was then added and the solution was cooled to 0–5 degrees Centigrade during the addition of 2 (9.46 g, 75.6 mmol) in dry 1,2-dichloroethane (25 mL). The mixture was then heated to reflux for 15 minutes. The reaction was cooled to room temperature, treated with a mixture of ethyl acetate (60 mL) and water (75 mL), poured into saturated $NaHCO_3$ (350 mL), and separated. The aqueous layer was washed three times with ether, and the combined organic extracts were washed twice with aqueous saturated $Na_2CO_3$, dried over $Na_2SO_4$, and evaporated under vacuum. The resulting solid was sublimed under reduced pressure ($20 \times 10^{-3}$ torr) at 60 degrees Centigrade in 3-hour intervals to yield compound 3 (7.79 g, 50.1 mmol, 66%). $^1$H-NMR ($CDCl_3$): δ 10.57 (br s, 1H), 9.70 (s, 1H), 6.95 (m, 2H), 3.94 (s, 3H).

1,4-bis(5-(methoxycarbonyl)-2-pyrryl)-1,4-butanedione (compound 4). A mixture of methyl 5-formylpyrrole-2-carboxylate (compound 3, 4.59 g, 30.0 mmol), 3-benzyl-5-(2-hydroxyethyl)-4-methyl-1,3-thiazolium chloride (1.23 g, 4.6 mmol), NaOAc (0.63 g, 7.7 mmol), and ethanol (40 mL) was heated at reflux temperature under argon. Divinyl sulfone (1.76 g, 14.9 mmol) was added dropwise, and the mixture was refluxed for another 17 hours. The resulting precipitate was filtered, washed with ethanol, water, and $Et_2O$ (each 25 mL). A yellowish white solid was obtained (4.49 g, 13.5 mmol, 90%). $^1$H-NMR ($CDCl_3$): δ 7.05 (m, 1H), 6.85 (m, 1H), 3.79 (s, 3H), 3.21 (s, 2H). $^{13}$C-NMR: δ 189.4, 160.5, 134.9, 126.7, 115.7, 115.4, 51.7, 32.2.

2,5-bis(5-(methoxycarbonyl)-2-pyrryl)thiophene (compound 5). A mixture of compound 4 (1.73 g, 5.2 mmol), dry toluene (75 mL), and Lawesson's reagent (1.50 g, 3.7 mmol) was refluxed under an argon atmosphere for 12 hours. The solution was cooled to room temperature and concentrated to one-third its original volume in vacuo. Methanol was added slowly to the toluene until a precipitate appeared. Column chromatography was performed using pure $CH_2Cl_2$ (silica gel; 230–400 mesh) as the initial eluant to remove impurities. Conversion to a 50:50 hexanes:EtOAc eluant system yielded 0.86 g (2.6 mmol, 50%) of a yellow solid. $^1$H-NMR ($CDCl_3$): δ 7.70 (s, 1H), 6.96 (dd, 1H), 6.52 (dd, 1H), 3.93 (s, 3H). $^{13}$C-NMR: δ 161.8, 134.0, 132.4, 125.7, 124.0, 117.8, 109.2, 52.2.

2,5-bis(5-(hydroxycarbonyl)-2-pyrryl)thiophene (compound 6). A mixture of compound 5 (1.56 g, 4.73 mmol), methanol (125 mL), NaOH (30 g) and $H_2O$ (80 mL) was refluxed. The reaction was cooled to room temperature and the methanol was removed under reduced pressure. The mixture was poured into ice water and acidified slowly using 1 M HCl until a solid precipitate resulted. Filtration and drying produced 1.29 g (4.3 mmol, 90%) of the green title compound. $^1$H-NMR (d-DMSO): δ 7.33 (s, 1H), 6.81 (dd, 1H), 6.37 (dd, 1H). $^{13}$C-NMR: δ162.2, 134.6, 132.0, 125.1, 124.4, 117.1, 108.8.

2,5-bis-(5-(3-hydroxy-propoxy carbonyl)-2-pyrrolyl) thiophene (compound 7). DBU (1,8-diazabicyclo[5.4.0] undecene-7) 1.29 g (8.46 mmol) was added dropwise over 10 minutes to a stirred solution of compound 6 (1.28 g; 4.23 mmol) in anhydrous DMSO (20 mL) under a nitrogen atmosphere. After the solution was stirred for 20 minutes, 1.77 g (12.70 mmol) of 3-bromo-1-propanol was added dropwise over 10 minutes and stirring was continued overnight at room temperature. The reaction mixture was poured into water and the precipitate was collected by filtration and washed thoroughly with water. The crude product was purified by chromatography (silica gel; 230–400 mesh; 30:70 hexanes:EtOAc) to yield compound 7 (1.08 g, 2.58 mmol, 61%). $^1$H-NMR (d-DMSO): δ 12.26 (s, 1H), 7.56 (s, 1H), 6.80 (d, 1H), 6.39 (d, 1 H), 4.56 (s, 1H), 4.27 (d, 2H), 3.52 (d, 2H), 1.82 (m, 2H). $^{13}$C-NMR: δ 160.38, 132.91, 131.21, 124.70, 123.21, 116.72, 108.28, 61.24, 57.42, 31.86.

Synthesis of Polymer (compound 8). To solution of compound 7 (1.20 g, 2.87 mmol) in dry pyridine (20 mL) was added to adipoyl chloride (0.525 g, 2.87 mmol) in anhydrous THF (2 mL) under a nitrogen atmosphere. The solution was refluxed overnight and the pyridine was evaporated under reduced pressure. Water was added to the residue and the solid was collected by filtration. After continued washing with water, the solid was added to boiling methanol, filtered, and dried in vacuo to afforded 0.89 g (1.72 mmol) of the polymer. $^1$H-NMR (d-DMSO): δ 12.22, 7.54, 6.81, 6.39, 4.26, 4.13, 2.25, 1.97, 1.48. $^{13}$C-NMR: δ 172.76, 160.15, 132.89, 131.31, 124.72, 122.97, 116.87, 108.28, 60.96, 60.74, 33.11, 27.86, 23.88.

The strategy for the synthesis of polymer 8 is outlined in SCHEME 1. Pyrrole was treated with trichloroacetyl chloride in ether to give compound 1 in 85% yield. The methyl ester of this compound (2) was formed by reacting compound 1 with sodium methoxide in refluxing methanol, achieving yields of 71%.

An aldehyde was inserted at the 5-position of compound 2 using Vilsmeyer conditions to form compound 3. During this synthesis, the 4-formyl isomer was produced in addition to the desired 5-formyl compound. Sublimation of the crude mixture at reduced pressures ($20 \times 10^{-3}$ torr) and 60 degrees Centigrade in 2.5-hour intervals yielded compound 3 in 67% yield.

Submission of compound 3 to Stetter conditions resulted in the 1,4-diketone compound 4, which precipitated from the cooled reaction mixture in 87% yield and high purity. Closure of compound 4 to the corresponding thiophene ring (compound 5) was accomplished in 50% yield using Lawesson's reagent in refluxing toluene. Base hydrolysis of the methyl ester groups provided compound 6 in 90% yield. Compound 6 was esterified to compound 7 (61%) using DBU (1,8-diazabicyclo[5.4.0]undecene-7) and 3-bromo-1-propanol in DMSO.

Figure 2:
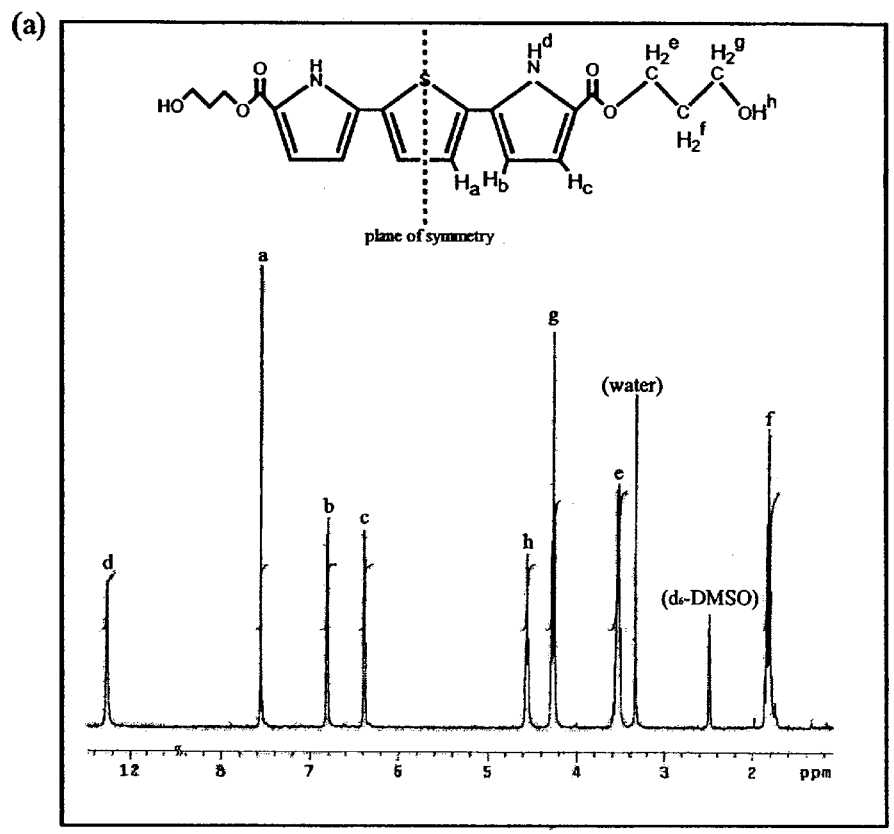
FIG. 2 depicts the proton nuclear magnetic resonance spectrum of (a) a monomer, and (b) a polymer, in accordance with the present invention.
Figure 2:
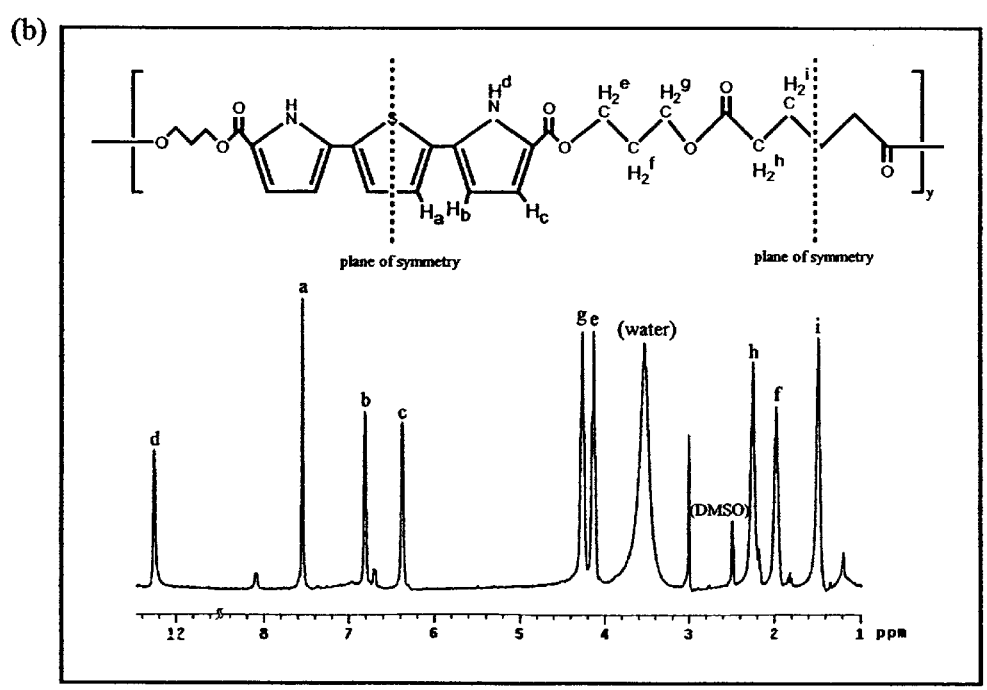
Figure 3:
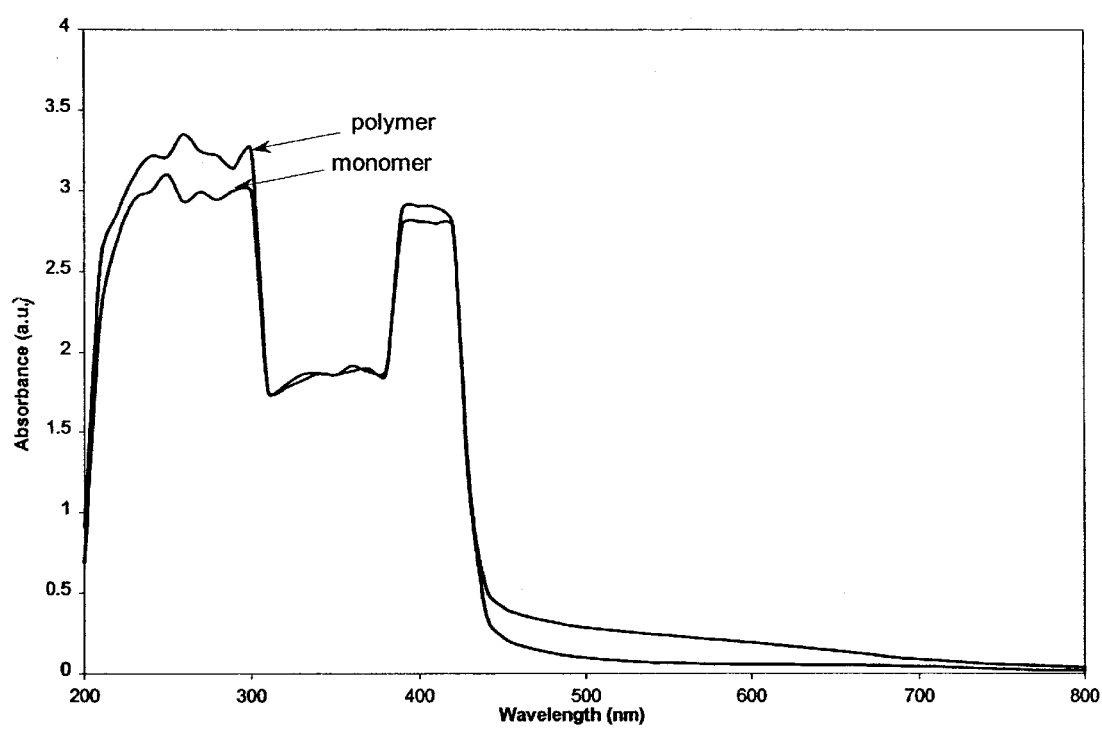
FIG. 3 depicts the UV-Visible absorbance spectrum of a monomer and a polymer in accordance with the present invention.

Polymer 8 was prepared in 60% yield by condensation of compound 7 with adipoyl chloride in refluxing pyridine under argon. $^1$H-NMR analysis of the monomer (compound 7; FIG. 2a) and the polymer (compound 8; FIG. 2b) revealed that the heteroaromatic segment was conserved during the polymerization process as indicated by the presence of the three peaks in aromatic region of the spectrum (6–8 ppm). The UV-visible spectrum of compounds 7 and 8 also confirmed the preservation of the aromatic region (FIG. 3) since there is little to no peak shifting from the monomer to the polymer. The purified polymer demonstrated good solubility in THF and GPC studies showed a band with a peak corresponding to a molecular weight of 8,500 and a polydispersity index of 3.0 using polystyrene as a reference.

Figure 4:
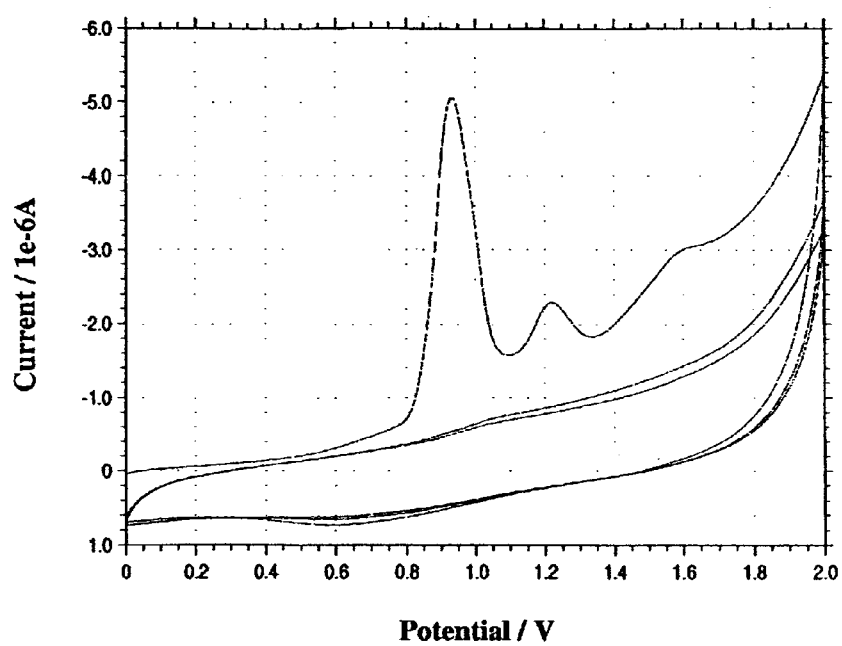
FIGS. 4 and 5 are a cyclic voltamagram and UV spectrum of a polymer in accordance with the present invention; and SCHEME 1 depicts the sequence of compounds synthesized in order to produce a polymer in accordance with the present invention, where a is $Cl_3COCl$; b is methanol, Na, reflux; c is $POCl_3$ (first) followed by $NaHCO_3$ (second); d is a thiazolium salt catalyst, NaOAc, divinyl sulfone, EtOH reflux; e is Lawesson's reagent, toluene reflux; f is NaOH, MeOH, $H_2O$, reflux; g is DBU, 3-bromo-1-propanol, DMSO; and h is adipoyl chloride, pyridine, reflux.

Conducting polymers and oligomers of polypyrrole and polythiophene require oxidation before electrical conduction can occur. Thus, cyclic voltammetry (CV) was used to determine the electrochemical properties of the polymer. As seen in FIG. 4, the polymer undergoes an irreversible oxidation at 0.96 V and 1.20 V (vs. SCE) after the first scan. To test if the irreversibility resulted from the polymer being overoxidized, CV scans were stopped just after the first (1.1 V vs. SCE) and second (1.3 V vs. SCE) peaks. The redox process was still not reversible. Conductivity measurements indicate that a current can be passed through the polymer when doped with iodine vapor.

Biocompatibility with cells is tested with human neuroblastoma cells. Cells were seeded onto a thin polymer film. The cells attached to the polymer surface and readily expressed their nerve-like phenotype by extending neurites. This attachment was seen after 1 day and continued after a week.

Figure 5:
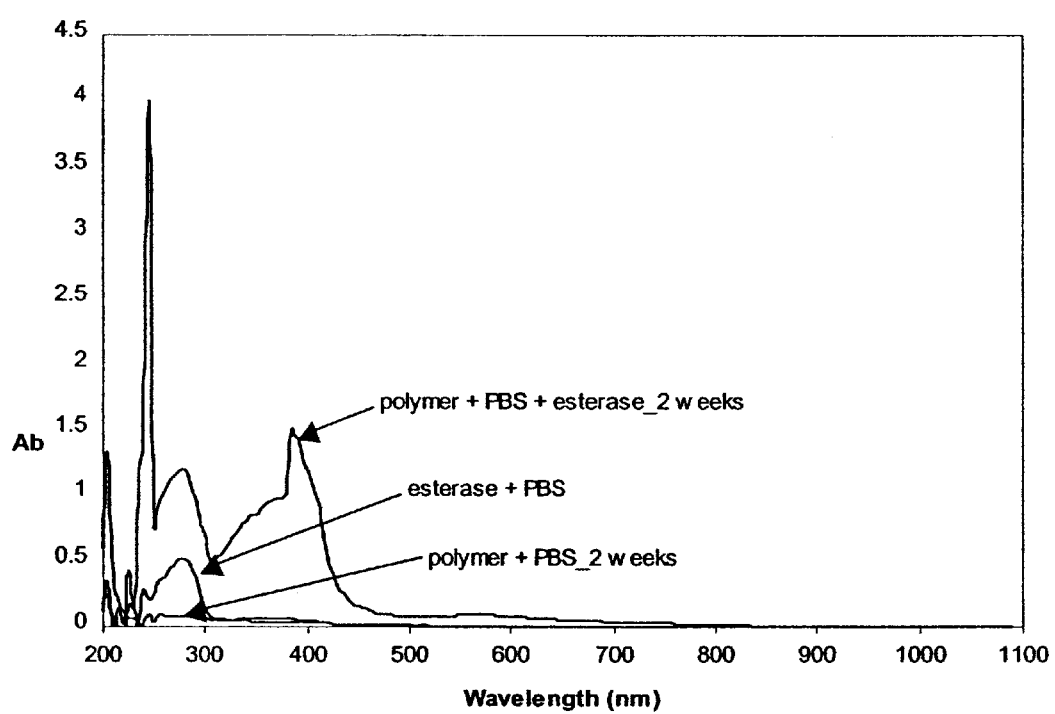

The biodegradability of the polymer was examined by UV-Visible spectroscopy of degradation studies in the presence of cholesterol esterase and in its absence. The results are depicted in FIG. 5. Without the esterase, there is no indication of degradation over a two-week period. In the presence of the esterase, the spectra indicate the presence of both monomer and polymer such that the polymer was undergoing biodegradation.

While specific alternatives to steps of the invention have been described herein, additional alternatives not specifically disclosed, but known within the art, are intended to fall within the scope of the present invention. Thus it is understood that other applications of the present invention will be apparent to those skilled in the art upon the reading of the described embodiments and a consideration of the claims and drawings.

What is claimed:

1. A chemical compound for use in a biodegradable electrically conducting polymer comprising the structure:

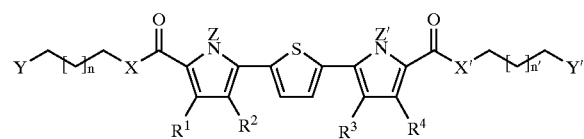

wherein n and n' independently=0 to 10; $R^1$, $R^2$, $R^3$ and $R^4$ are each independently a substituent selected from the group consisting of hydrogen, alkyl, aryl, halogen, hydroxyl, and carboxyl, or a salt thereof; X and X' are independently oxygen or nitrogen atoms that form ester or amido linkages respectively; and Y and Y' are independently a OH or a $NH_2$ substituent; and Z and Z' are each independently a substituent selected from the group consisting of hydrogen, alkyl, aryl, halogen, hydroxyl, and carboxyl, or a salt thereof.

2. The chemical compound recited in claim 1, wherein n and n' are equal to 1.

3. The chemical compound recited in claim 1, wherein $R^1$, $R^2$, $R^3$, $R^4$, Z and Z' are each a hydrogen atom.

4. The chemical compound recited in claim 1, wherein $R^1$, $R^2$, $R^3$, and $R^4$ are each independently selected from methyl, ethyl, propyl, butyl, decyl, cyclohexyl, methoxy, ethoxy, phenyl, benzyl, tolyl, chloride, bromide, and iodide and the like.

5. The chemical compound recited in claim 1, wherein Z and Z' are each independently selected from the group of substituents consisting of methyl, ethyl, propyl, butyl, decyl, cyclohexyl, methoxy, ethoxy, phenyl, benzyl and tolyl.

6. The chemical compound recited in claim 1, wherein X and X' are oxygen atoms.

7. The chemical compound recited in claim 1, wherein Y and Y' are OH groups.

8. The chemical compound recited in claim 1, wherein X and X' are alkyl or aryl substituted nitrogen atoms.

9. The chemical compound recited in claim 1, further comprising a bioactive compound.

10. The chemical compound recited in claim 9, wherein the bioactive compound is selected from the group consisting of a drug, a protein, a peptide, a polysaccharide, an oligonucleotide, a synthetic organic molecule, and a synthetic inorganic molecule.

11. The chemical compound recited in claim 9, wherein the bioactive compound is selected from the group consisting of a therapeutic, prophylactic, and diagnostic agent.

12. The chemical compound recited in claim 1, wherein the chemical compound is delivered to the body in the form of a structure selected from the group consisting of sutures, tubes, sheets, films, and scaffolds for tissue engineering.

13. The chemical compound recited in claim 1, wherein the chemical compound further comprises a polymer blend with one or more covalently and ionically crosslinkable or hydrophilic polymers.

14. The chemical compound recited in claim 13, wherein the polymer blend is selected from the group consisting of one or more synthetic polymers of poly(ethylene glycol), poly(ethylene oxide), partially or fully hydrolyzed poly(vinyl alcohol), poly(vinylpyrrolidone), poly (ethyloxazoline), poly(ethylene oxide)-co-poly(propylene oxide) block copolymers (poloxamers and meroxapols), poloxamines, carboxymethyl cellulose, and hydroxyalkylated celluloses such as hydroxyethyl cellulose and methylhydroxypropyl cellulose, and natural polymers such as polypeptides, polysaccharides or carbohydrates such as Ficoll®, polysucrose, hyaluronic acid, dextran, heparan sulfate, chondroitin sulfate, heparin, and alginate, and proteins such as gelatin, collagen, albumin, and ovalbumin, other copolymers, and combinations thereof.

15. The chemical compound recited in claim 1, wherein the chemical compound is mixed with any combination of at least one or more bioactive compound, one or more cell type, and one or more polymer blend.

16. The chemical compound recited in claim 15, wherein the cell type is obtained from a donor, from cell culture of cells from a donor, or from cell culture.

17. The chemical compound recited in claim 15, wherein the cell type is selected from a group consisting of a chondrocyte, osteoblast, muscle cell, thyroid cell, parathyroid cell, immune cell, pancreatic cell, fibroblast, hepatocyte, epithelial cell, islet cell, nerve cell, and other cells acting primarily to synthesize and secrete or metabolize materials.

18. The chemical compound recited in claim 15, wherein the cell type is genetically altered, a cell line or cell clone obtained from the intestines, kidney, heart, brain, spinal cord, muscle, skeleton, liver, stomach, skin, lung, reproductive system, nervous system, immune system, spleen, bone marrow, lymph nodes, glands, and combinations thereof.

19. A biodegradable conducting polymer for tissue engineering comprising:

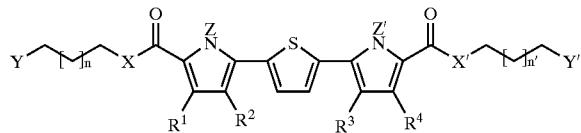

wherein n and n' independently=0 to 10; $R^1$, $R^2$, $R^3$ and $R^4$ are each independently a substituent selected from the group consisting of hydrogen, alkyl, aryl, halogen, hydroxyl, and carboxyl, or a salt thereof; X and X' are independently oxygen or nitrogen atoms that form ester or amido linkages respectively; and Y and Y' are independently a OH or a $NH_2$ substituent; and Z and Z' are each independently a substituent selected from the group consisting of hydrogen, alkyl, aryl, halogen, hydroxyl, and carboxyl, or a salt thereof.

20. The biodegradable conducting polymer for tissue engineering recited in claim 19, wherein the biodegradable conducting polymer is delivered to the body in the form of a structure selected from the group consisting of sutures, tubes, sheets, films, and scaffolds.

21. The biodegradable conducting polymer for tissue engineering recited in claim 19, further comprising a bioactive compound selected from the group consisting of a drug, a protein, a peptide, a polysaccharide, an oligonucleotide, a synthetic organic molecule and a synthetic inorganic molecule.

22. The biodegradable conducting polymer for tissue engineering recited in claim 19, further comprising a cell type selected from the group consisting of a genetically altered cell, a cell line, or cell clone from the intestines, kidney, heart, brain, spinal cord, muscle, skeleton, liver, stomach, skin, lung, reproductive system, nervous system, immune system, spleen, bone marrow, lymph nodes, glands, and combinations thereof.

23. The biodegradable conducting polymer for tissue engineering recited in claim 19, further comprises a polymer blend selected from the group consisting of one or more covalently and ionically crosslinkable or hydrophilic polymers.

24. The biodegradable conducting polymer for tissue engineering recited in claim 23, wherein the polymer blend further comprises one or more synthetic polymers of poly(ethylene glycol), poly(ethylene oxide), partially or fully hydrolyzed poly(vinyl alcohol), poly(vinylpyrrolidone), poly(ethyloxazoline), poly(ethylene oxide)-co-poly(propylene oxide) block copolymers (poloxamers and meroxapols), poloxamines, carboxymethyl cellulose, and hydroxyalkylated celluloses such as hydroxyethyl cellulose and methylhydroxypropyl cellulose, and natural polymers such as polypeptides, polysaccharides or carbohydrates such as Ficoll®, polysucrose, hyaluronic acid, dextran, heparan sulfate, chondroitin sulfate, heparin, and alginate, and proteins such as gelatin, collagen, albumin, and ovalbumin, other copolymers, and combinations thereof.

25. The biodegradable conducting polymer for tissue engineering recited in claim 19, wherein the biodegradable conducting polymer is implanted in a mammal.

26. The biodegradable conducting polymer for tissue engineering recited in claim 19, wherein the biodegradable conducting polymer is incorporated into a suture, a tube, a sheet, an adhesion prevention device, a wound healing device, a tissue healing agent or a cell growth promoter that enhance the biocompatibility of the biodegradable conducting polymer.

27. The biodegradable conducting polymer for tissue engineering recited in claim 19, wherein the biodegradable conducting polymer is used for transplant engraftment, tissue regeneration, tissue repair, tissue reconstruction, tissue growth, tissue differentiation, limb reattachment, limb reconstruction, immunogenic response, cognitive function, and combinations thereof.

28. The biodegradable conducting polymer for tissue engineering recited in claim 19, wherein its function is selected from the group consisting of regenerative, restorative, reconstructive, therapeutic, prophylactic, and diagnostic.

29. A biodegradable conducting polymer comprising the chemical compound recited in claim 1 coupled with any combination of at least one or more bioactive compounds for the delivery of drugs or other biologically active molecules in a mammal.

30. The biodegradable conducting polymer recited in claim 29, wherein the biodegradable conducting polymer further comprises a polymer blend with one or more covalently and ionically crosslinkable or hydrophilic polymers selected from the group consisting of one or more synthetic polymers of poly(ethylene glycol), poly(ethylene oxide), partially or fully hydrolyzed poly(vinyl alcohol), poly(vinylpyrrolidone), poly(ethyloxazoline), poly(ethylene oxide)-co-poly(propylene oxide) block copolymers (poloxamers and meroxapols), poloxamines, carboxymethyl cellulose, and hydroxyalkylated celluloses such as hydroxyethyl cellulose and methylhydroxypropyl cellulose, and natural polymers such as polypeptides, polysaccharides or carbohydrates such as Ficoll®, polysucrose, hyaluronic acid, dextran, heparan sulfate, chondroitin sulfate, heparin, and alginate, and proteins such as gelatin, collagen, albumin, and ovalbumin, other copolymers, and combinations thereof.

31. A method for preparing a chemical compound for use in biodegradable conducting polymers comprising the steps:

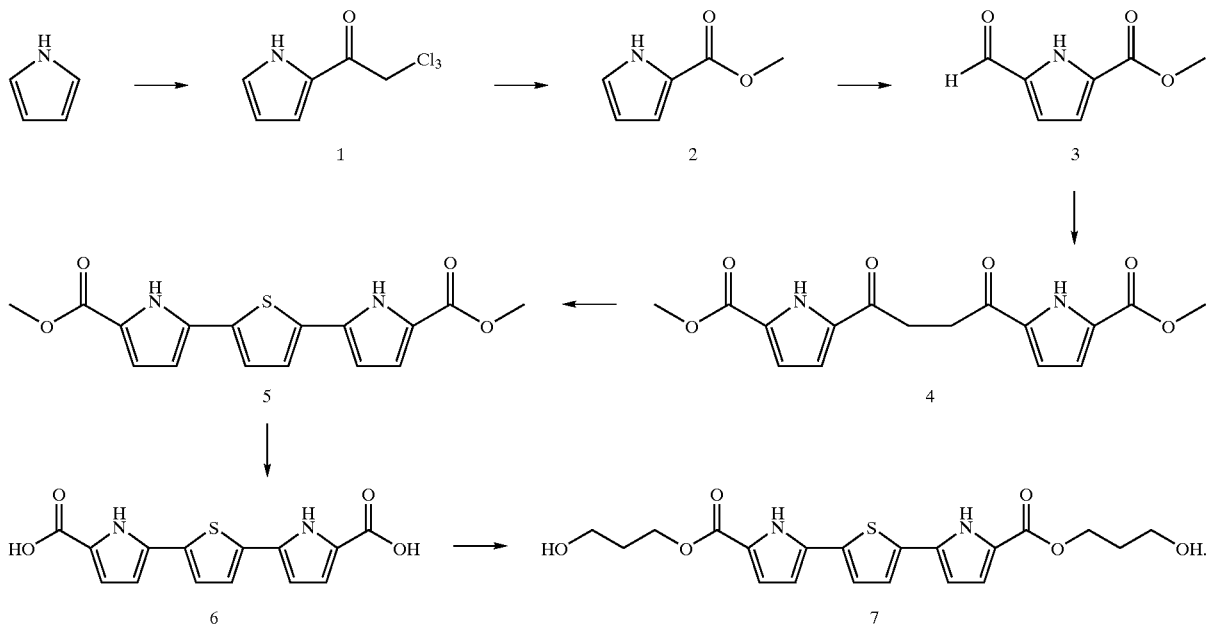

32. The method recited in claim 31, wherein compound 1 is synthesized by treatment of pyrrole with trichloroacetyl-chloride.

33. The method recited in claim 31, wherein compound 2 is synthesized by treatment of compound 1 with sodium methoxide in refluxing methanol.

34. The method recited in claim 31, wherein compound 3 is produced by treatment of compound 2 with phosphoryl chloride in dimethylformamide.

35. The method recited in claim 31, wherein compound 4 is produced by treatment of compound 3 with sodium acetate, divinyl sulfone, and a thiazolium salt catalyst in refluxing ethanol.

36. The method recited in claim 31, wherein compound 5 is produced by treatment of compound 4 with Lawesson's reagent in refluxing toluene.

37. The method recited in claim 31, wherein compound 6 is produced by treatment of compound 5 with a refluxing mixture of methanol and water containing sodium hydroxide.

38. The method recited in claim 31, wherein compound 7 is produced by treatment of compound 6 with DBU and 3-bromo-1-propanol in dimethylsulfoxide.

39. A biodegradable conducting polymer produced by the method as recited in claim 31.

* * * * *

UNITED STATES PATENT AND TRADEMARK OFFICE
CERTIFICATE OF CORRECTION

PATENT NO. : 6,696,575 B2
APPLICATION NO. : 10/107705
DATED : February 24, 2004
INVENTOR(S) : Christine E. Schmidt and Tyrell J. Rivers It is certified that error appears in the above-identified patent and that said Letters Patent is hereby corrected as shown below:

At Column 1, at or about lines 7-9:

-replace the lines with what is written below:

"This invention was made with government support under 9702882 awarded by the National Science Foundation. The government has certain rights in the invention."

Signed and Sealed this

Seventeenth Day of November, 2009

David J. Kappos
*Director of the United States Patent and Trademark Office*